United States Patent [19]

Deleeuw

[11] Patent Number: 5,576,781
[45] Date of Patent: Nov. 19, 1996

[54] DISPOSABLE CAMERA

[76] Inventor: Paul Deleeuw, 181 Crandon Blvd., #301, Key Biscayne, Fla. 33149

[21] Appl. No.: 243,371

[22] Filed: May 16, 1994

[51] Int. Cl.$^6$ .................................................. G03B 17/08
[52] U.S. Cl. .................................. 396/6; 396/14; 396/17; 396/25
[58] Field of Search ............................. 354/62, 64, 295, 354/286

[56] References Cited

U.S. PATENT DOCUMENTS

| | | | |
|---|---|---|---|
| 2,951,429 | 9/1960 | Leong | 354/295 |
| 4,297,017 | 10/1981 | Farmer | 354/62 |
| 4,522,196 | 6/1985 | Cunningham et al. | 354/62 |
| 4,766,451 | 8/1988 | Fujimura et al. | 354/64 |
| 4,882,600 | 11/1989 | Van de Moere | 354/64 |
| 4,967,214 | 10/1990 | Taniguchi et al. | 354/295 |
| 5,010,876 | 4/1991 | Henley et al. | 354/62 |

Primary Examiner—David M. Gray
Attorney, Agent, or Firm—Bachman & Lapointe, P.C.

[57] ABSTRACT

A disposable and disinfected still frame camera for use in contamination sensitive areas includes an inner camera portion for securing still frame film, exposing frames of the film and for advancing the film. A camera housing is also provided for enclosing the inner camera portion. The invention also includes a fluid impervious casing which substantially encases the camera housing for protecting the camera and environment from contamination. The disposable camera may also include attachments for connecting the camera to optical medical devices, a measuring device for measuring the distance between the camera lens and the object being photographed, and sterilized or disinfected packaging.

17 Claims, 2 Drawing Sheets

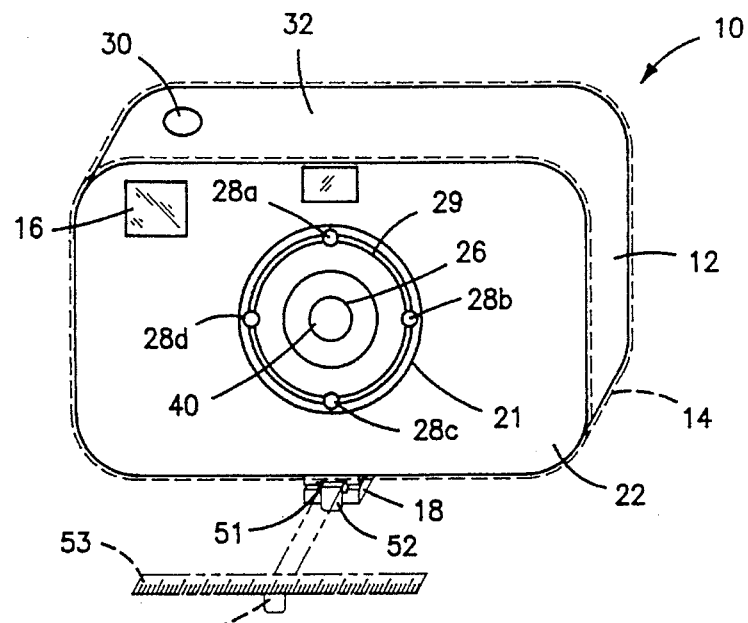
FIG-1
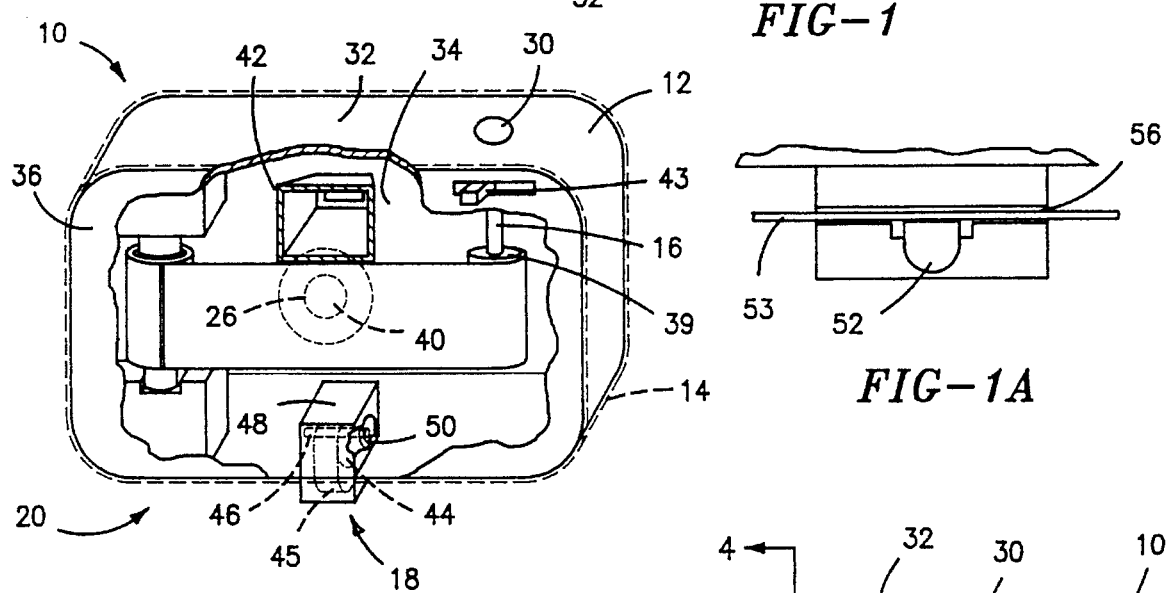
FIG-2
FIG-1A
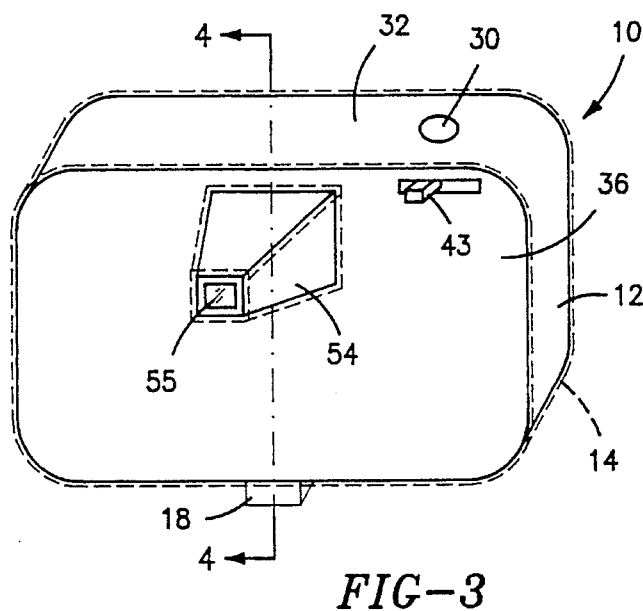
FIG-3

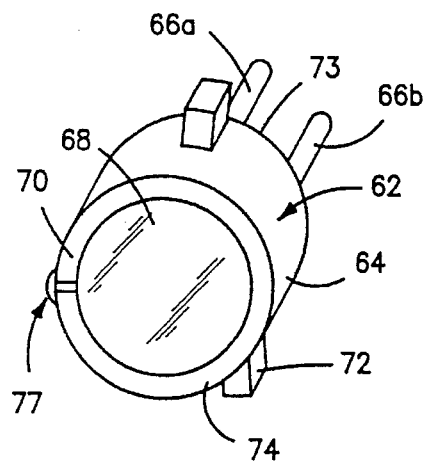
FIG-6
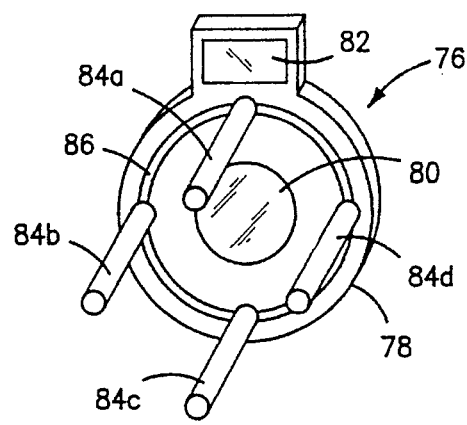
FIG-9
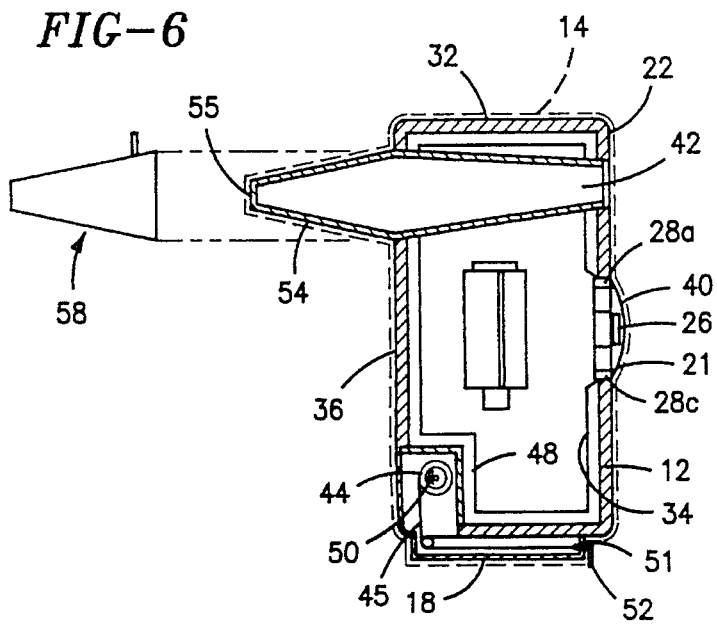
FIG-4
FIG-5
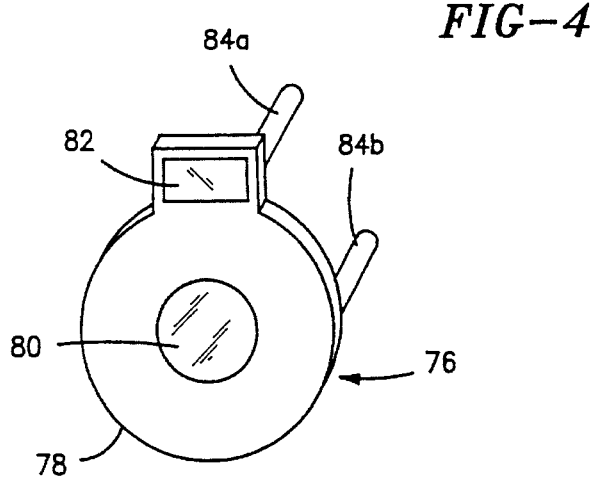
FIG-8
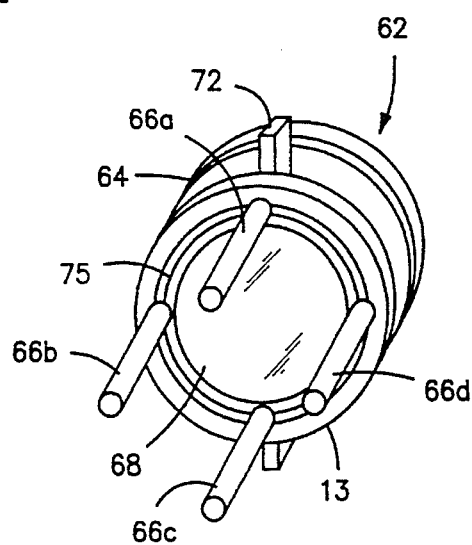
FIG-7

DISPOSABLE CAMERA

BACKGROUND OF THE INVENTION

The present invention is directed toward disposable cameras, and more particularly, to a disposable and disinfected still frame camera for use in contamination sensitive areas.

In the medical field, physicians or the like use photographs and videos as documentation, for legal uses, to display their work or for use as teachings aids. Frequently, the objects of the photography and/or the procedure being photographed are located in sensitive environments requiring strict attention to disinfection and sterilization. Any instruments used in such environments must be sterilized or disinfected to industry standards. Any video or photography equipment, therefore, used in the operating room or the like, must also be disinfected. Unfortunately, frequent sterilization or disinfection using chemicals and/or radiation tend to eventually effect the functional capacity of video or photography equipment. If delicate electronic circuits are exposed to radiation or chemicals, such circuits can be ruined, and frequently, the entire video or photographic system can be damaged. Accordingly, it would be beneficial to use a disposable video or photography system which needs only to be sterilized or disinfected once, preferably on the manufacturing floor, and packaged in a sterilized or disinfected manner. As such, the camera can be disposed of after being used in the sterilized or disinfected environment, negating the need for further sterilization after its one use.

There exists disposable cameras which are directed to the consumer use market. That is, such cameras are not properly designed for the reduction of contaminable trouble spots nor are they disinfected or include other important features preferable for use in sensitive areas such as hospital operating rooms. The prior art does disclose a video camera system having a disposable camera portion which is adapted to be disinfected prior to use in sensitive areas such as hospital operating rooms.

U.S. Pat. No. 5,010,876 to Henley et al. discloses a system directed toward endoscopic surgical practice. The patent discloses a method and apparatus for providing a disposable, sterilized cable connector and camera head unit for use in endoscopic surgery. The camera head and circuitry are directed for use in videography. The camera head and cable are operatively arranged in a sterilized removable package. At the point of use, the package is removed and the unit can be easily connected and disconnected to a camera control unit. During manufacturing, the camera head and cable are sterilized and arranged in the compact and disposable unit. Accordingly, after use in the contaminable area, the unit can be disposed of, thereby negating the need for subsequent sterilization. Unlike the instant invention, the sterilized camera head and cable unit are directed towards videography and not still framed photography. Accordingly, relatively complex circuitry and control units as well as monitors and recorders are necessary to use the disposable unit. The system disclosed in Henley is therefore, too complex for use in still framed photography. More importantly, the sterile packaging used in Henley is removed before installing the unit in the sensitive environment.

U.S. Pat. No. 5,146,256 to Frosig et al. discloses a disposable camera having a close-up attachment. The Frosig et al. disposable camera is similar to the commercial disposable cameras found on the market today. The invention is directed mainly to a close-up camera attachment used for magnifying the object of the picture. The close-up attachment is a plug-like insert which can be manually positioned in an open view finder tunnel of the camera. The Frosig patent does not disclose the sterilization of any portion of the camera, and has no coating, layer or the like on the housing of the camera for making the same disinfected. Accordingly, the Frosig et al. invention would not be applicable for use in highly sensitive areas.

U.S. Pat. No. 4,973,998 to Gates discloses a disposable single use camera having a reusable electronic flash unit for snap attachment to the camera. Again, and similar to the camera disclosed in the Frosig et al. patent, the camera portion of this invention is simply a disposable camera unit which is preloaded with film. In accordance with the actual invention, the inner camera part includes an engagable locator means for connecting the camera to a flash unit which includes a positioning means. The Gates disposable camera does discuss an outer sealed pack for housing the inner camera portion. However, this outer seal pack does not serve the purpose of sterilization or disinfection of the camera, it is directed towards an economical mode of housing the inner camera portion.

As to measuring devices connected with cameras, U.S. Pat. No. 4,836,671 to Bautista discloses a locating device. The invention relates to a device for determining the location of a point, line or plane with respect to an object. The invention is directed for use, in one embodiment, with the radiography profession where it is necessary to know the location of an x-ray film cassette relative to an object such as an x-ray generator. The device includes a beam generator which adapted to be coupled to the object to which relative location is desired. The device generates a plane of light containing the axis of projection of the object. The beam generator also generates a second ray of light oriented at an angle to the axis of projection so as to intercept the same at the point to be located. This point is then marked by a second beam generator. The locating device disclosed in Bautista is far to complicated for use with the disposable and economical camera systems.

Hence, there exists a need in the medical care field for a disposable and disinfected still frame camera which can be used in areas which are highly sensitive to contamination and which has features such as a flash unit, a close-up attachment lens, and a measuring device as well as other features which will become apparent in the following description.

SUMMARY OF THE INVENTION

The primary object of this invention is to provide a disinfected and disposable still frame camera which may be safely used in areas which are highly sensitive to contamination.

Another object of this invention is to provide a disposable and disinfected still frame camera which includes connections for converting and attaching the camera to optical medical instruments for using the camera for taking photographs of generally inaccessible areas.

A further object of this invention is to provide a disposable and disinfected still frame camera which is inexpensive to manufacture and purchase, while still including all necessary features.

A still further object of this invention is to provide a disposable and disinfected photographic system which includes a disposable and disinfected still framed camera, a protective disinfected casing around the camera, and a sterilized or disinfected package.

Additional objects of this invention will be apparent from the following description.

The foregoing objects are obtained by the inventive disposable still frame camera of the instant invention which broadly includes an inner camera portion means for securing still frame film, exposing frames of the film and advancing the film; a camera housing used for enclosing the inner camera portion; and a fluid impervious casing means which substantially encases the camera housing for protecting the camera and the environment from unwanted contamination.

The inventive camera preferably also include disposable view finder cap means for engaging a view finder means in order to protect the camera from contamination via human facial contact; adaptor means for attaching the camera housing to optical medical instruments and for converting the optics of the medical instruments for compatibility with the optics of the inventive disinfected camera; and measuring means for measuring the distance of the object of the photography from the inventive camera.

One embodiment of the present invention includes the inner camera portion means comprising a lens arrangement and advancing mechanism for exposing film and advancing the same. The same embodiment also preferably includes the camera housing means comprising a substantially smooth and continuous housing which is preferably disinfected. The embodiment preferably also includes the disinfected casing means comprising a transparent flexible plastic for entirely covering the housing, and which may be disinfected in solutions for maintaining the sterility of the camera for placement in a sterile field.

This embodiment may also include the adapter means being an endoscope connector for attaching the camera to the lens of an endoscope and for converting the optics of the scope for compatibility with the optics of the camera. This embodiment may also include the measuring means comprising a measuring tape and reel which is preferably integrally connected to the housing and which extends therefrom for measuring the distance between the camera lens and the object being photographed and for displaying a measuring device to illustrate specimen size.

The details of the present invention are set out in the following description and drawings wherein like reference characters depict like elements.

BRIEF DESCRIPTION OF THE DRAWINGS

FIG. 1 is a front perspective view of a disposable disinfected camera in accordance with the present invention.

FIG. 2. is a rear perspective cut-away view of the camera showing the internal mechanisms of the camera in accordance with the present invention.

FIG. 3 is a rear perspective view of the disposable disinfected camera including a view finder in accordance with the present invention.

FIG. 4 is a cross sectional view of the camera taken along line 4—4 of FIG. 3.

FIG. 5 is a perspective view of a view finder cover used for engagement with the view finder shown in FIG. 3.

FIG. 6 is a front perspective view of an adapter and converter for allowing use of the camera with optical medical devices.

FIG. 7. is a rear perspective view of the adaptor and converter shown in FIG. 6.

FIG. 8 is a front perspective view of a close up lens attachment.

FIG. 9 is a rear perspective view of the close up lens attachment shown in FIG. 8.

DETAILED DESCRIPTION

Referring now to the drawings in detail, there is shown in FIG. 1 a perspective view of a disposable and disinfected still frame camera constructed in accordance with the principles of the present invention and designated generally as 10. The disposable and still framed camera of the instant invention is designed to be economically manufactured so that the camera can be operable for a single use, which includes using the roll of film provided with the camera, and then disposed. As shown in FIG. 1, disinfected disposable still frame camera 10 generally includes a camera housing 12, an outer casing material 14, a flash unit 16, a measuring device 18, and as shown in FIG. 2, an inner camera mechanism 20.

Referring still to FIG. 1, camera housing 12 is preferably constructed from a cardboard or plastic material. The shape of camera 10 substantially resembles that of a rectangular box. Advantageous to disinfection and sterilization and maintenance of the same, the housing 12 should be generally smooth and continuous, having a minimal amount of creases or grooves which may trap contaminants. Camera 10 may preferably be of a size which is convenient and ergonomic for placement in the average size hand. As shown in the figures, the corners and edges of camera 10 are preferably rounded so as to avoid potential chipping or the like which may result in grooves that can become contaminated. This preferable smooth and continuous design of housing 12 will assist in providing a disposable camera free of high risk contamination areas, a feature not found in the prior art disposable type cameras.

Housing 12 also includes a lens containment portion 21 located on the front center portion of the camera 10 which houses a camera lens system. Lens containment portion 21 is preferably formed or molded with the rest of the camera and includes a central opening 26 for engagement with the lens system. Adjacent lens containment portion 21 are preferably four holes 28a–28d which extend into the front surface 22, perpendicular to the same and a circular ridge 29 which extends from the front surface 22. Holes 28a–28d are used to engage additional attachments for using camera 10 with optical medical instruments or for close up photography, which will be discussed below. As shown in FIG. 1, housing 12 will also include a built in flash unit 16 in the upper left corner of camera 10 and a photographing button 30 near flash unit 16.

Housing 12 may simply be that of disposable cameras currently on the market. A significant aspect of any housing used, however, is that it is susceptible to coverage by casing 14.

The inside of camera 10 includes an inner shell 34, constructed from an absorbent material such as cardboard or the like, which is preferably shaped to include various surfaces or the like for engaging inner camera portion 20 of the camera. Because inner camera portion 20 must be assembled into inner shell 34 of camera 10, the back wall 36 will preferably be formed separately from housing 12 and glued or otherwise fused to housing 12 for protection of the inner camera mechanism. Based again on the desire to reduce the possibility of contamination, it is preferable that back wall 36 be attached to housing 12 in a smooth and continuous manner. This may require a surface reducing step or material adding step, for smoothing down any grooves which may result or for filling any such grooves which may result, respectively. Also, because of the enclosed state of the inner camera portion, the absorbent inner shell 34 should be treated with fungicide for reducing fungal growth.

Referring now to FIG. 2, inner camera portion 20 is preferably comprised of elements which allow for a single use, point and shoot type camera. Inner camera portion 20 comprises inner camera shell 34 which houses the lens system, comprised of a fixed focused taking lens 40, a view finder tunnel 42 and a film winding mechanism 39, including a winding wheel 43. As an alternative, inner camera portion 20 may include a mechanical auto advance for advancing the film. Further details of disposable single use cameras which have inner camera portions which can be used for the present invention, are disclosed in U.S. Pat. Nos. 4,801,957, issued Jan. 31, 1989; 4,903,058, issued Feb. 20, 1990; and 4,973,998, issued Nov. 7, 1990. The significant differences between the inner camera portions disclosed in these patents and inner camera portion 20 of this patent including the elements discussed, are (1) lens 40 of the instant camera is preferably designed to focus at approximately 2'6" and (2) inner camera portion 20 including, i.e., inner camera shell 34, view finder tunnel 42 and lens 40 are preferably disinfected or assembled in a sterilized or disinfected environment at the point of manufacture. The sterilization process will be discussed below.

Referring still to FIGS. 1 and 2, camera 10 also includes a novel measuring device 18 used for measuring the distance of lens 40 from the object of the photograph. Measuring device 18 includes a spring loaded measuring tape reel 44, having a tape measure 45 wound thereon. The reel 44 is rotatably mounted to an axle 46 which is secured to a tape housing 48 which is secured to inner camera shell 34. Housing 48 is preferably box shaped having a slot extending half way down the center of the side walls thereof for engaging axle 46. Spring loaded reel 44 includes a spring device 50 which provides a force which opposes the pulling of tape measure 45 off the tape measure reel 46. Tape measure 45 extends out of tape measure housing 48 and into the exit slot 51, shown in FIGS. 1 and 4, and includes a hooked member 52, extending perpendicularly downward to tape measure 45 which engages the outer portion of tape measure device 18 as shown in FIG. 1. In addition, a substantially horizontally extending cross measuring piece 53 is attached to the end of tape measure 45 above hooked member 52, as shown in FIGS. 1 and 4. Cross piece 53 is used to measure the width or length of objects to be photographed and has distance measuring markings thereon in the form of centimeters, inches, or the like. Above exit slot 51, tape measure housing 48 has a recessed slot 56, extending horizontally, for receiving cross piece 53 upon the retraction of tape measure 45. As such, measuring tape 45 remains abutted against the exterior of camera 10 for access by the user to measure the appropriate distances. After pulling the tape 45 outward from reel 44, as shown via dotted lines in FIG. 1 and measuring the distance, the reel will retract the tape measure via spring device 50. Accordingly, a simple, convenient and integral device for measuring the distance of the object from the camera lens and its size for assuring top quality results is provided.

Flash unit 16 and picture button 30 are each typical of those used on disposable type cameras such as that manufactured by Fuji Photo Film Co. Ltd. The flash unit and button are electrically connected so as to synchronize the energization of the flash upon the pressing of the button.

Referring now to FIG. 3, the formation of the rear wall of the housing 12 also includes the formation of a view finder 54. View finder 54 has the shape of a four-sided figure with a broad base and a narrow top. In this case, the broad base is attached to or formed with back wall 36 and the narrow top extends outward towards the user of the camera.

View finder 54 preferably includes a substantially hollow body portion and a viewing portion 55 which is preferably in alignment with view finder tunnel 42, comprising a part of inner camera portion 20. Viewing portion 55, at the narrow end of view finder 54 is preferably a rectangular opening which may engage a transparent piece of glass, lens, other transparent material or may remain open. As with the rest of housing 12, the view finder is preferably covered with shrink wrap 14. Unlike prior art disposable cameras, with view finder 54 extending out as such, the eye fluids of the user of the camera are kept farther from the remaining portions of the camera.

Referring now to FIGS. 1–4, casing material 14 is shown by the dotted lines around the edges of camera 10 and is preferably formed from a transparent plastic material which allows light to pass therethrough. Transparent casing 14 is preferably thin and water tight and comprised of a plastic which is highly susceptible to sterilization. As can be seen from the figures, wrap 14 permanently covers the entire outer portion of housing 12 including lens 40, flash unit 16, view finder opening 55, but not exit slot 51. Casing 14 is flexible, allowing the pressing of buttons for shutter tripping and film advance. Also, casing 14 has minimal projections and folds for minimizing contaminations.

Referring now to FIG. 5, view finder cover 58 is preferably similar in shape and construction to view finder 54 and formed from a transparent material. View finder cover 58 functions to cover view finder 54 and therefore has a hollow inner portion similar in size to the outer surface of view finder 54. The inner portion is sized such that cover 58 can be force fit over view finder 54 such that the end of cover 58 is spaced from the end of view finder 54. The ends of cover 58 are both open, allowing the user to look through viewing portion 55 while cover 58 is installed. Cover 58 includes a resilient tab 60 which extends upwardly from cover 58 and is easily accessible for use by a user to disengage cover 58 from its force fit with view finder 54.

View finder cover 58 is also preferably disinfected and functions to separate the eye fluids of the user from the actual view finder via the space between the end of cover 58 and the end of view finder 54, unlike the prior art view finders having no cover and being set into the body of the camera. Accordingly, view finder cover 58 should be placed over view finder 54 so that contact between the user of the camera 10 and the actual view finder of the camera is avoided, thus avoiding possible contamination via eye fluids, and in operating rooms or the like, contamination of the camera via surgical masks. The camera may be provided with a number of view finder covers which are also disinfected at the point of manufacturing.

Referring now to FIGS. 6 and 7, a perspective view of an optical medical instrument adapter and converter is shown. The adapter and converter shown here functions to allow camera 10 to be used with an investigative optical medical device such as an endoscope. However, various shaped adapters having various connector designs are contemplated herein for use with this camera and other optical medical devices.

Adapter and converter 62 includes an outer ring shaped body portion 64 and alignment rods 66 formed preferably from plastic or the like, an optic conversion lens 68 and a connector clamp 70. Ring shaped body portion 64 should be of a sufficient length for allowing the manipulation of camera 10 adjacent an optical medical instrument such as an endoscope. Ring shaped body portion 64 also includes tabs 72 attached to the circumference thereof for assisting in opening the clamp 70 upon squeezing the tabs. The connecting clamp 70, preferably a circumferentially expanding iris clamp, attached to and adjacent front end 74, is used for connecting the adapter to the endoscope or other medical instruments. Connector rods 66a–66d are attached to the adapter and extend outwardly from the back end 73 of body portion 64 along the circularly shaped thickness thereof. Preferably, four rods 66a–66d extend from the back end and are spaced evenly thereon.

Conversion lens 68 is preferably connected to and centered on the front end portion 74 of body portion 64. Conversion lens 68 has optical properties which function to convert the optics of the endoscope, or other optical medical instruments, into optics compatible with the lens system of camera 10. That is, because the camera lens is designed to focus at 2'6" it is preferable that the conversion lens 68 have an infinite focus.

The adapter is preferably connected to camera 10 via rods 66a–66d by inserting the rods into holes 28a–28d on the front surface 22 of camera 10. Adapter 62 also includes a ridge 75 formed within the back end 73 which engages groove 29, formed on lens containment portion 21 for aligning adapter 62 thereon and causing a sealed fit. Accordingly, unlike the prior art, disposable still frame camera 10 can be used to take photographs of the areas to which endoscopes or other optical medical instruments are used for access.

Referring now to FIG. 8, disposable and disinfected camera 10 may also include a close-up attachment 76 which functions to magnify the object of the photograph for obtaining close up pictures. The attachment includes a frame 78, a close up lens 80, a view finder lens 82 and connecting rods 84a–84d. Lens 80 should be optically designed to be placed adjacent lens 40 of camera 10 for focusing on the object of the photograph at a much closer range than with the lens 40. Preferably, the close up lens 82 will focus at approximately 14" and expose about 7" of the object. The proper distance of the camera relative to the object can be calculated via the measuring device 18, to assure ideal exposure.

The lens is preferably situated in frame 78 wherein frame 78 has connecting rods 84a–84d extending from the rear side thereof which engage the holes 28a–28d in the camera housing 12, similar to the optical instrument adapter 62. Also, similar to adapter and connector 62, the frame has a ridge 86 for insertion into groove 29 of camera 10 to achieve alignment and a proper seal. Supplemental view finder lens 82 extends upwardly from the top of the frame 78 for alignment with the view finder tunnel 42. The lens 82 includes optical properties which function to cause viewing through view finder 54 to correspond to close up lens 80. Because of the lens 82, the photographer is allowed to see a close up image of the object, similar to that seen through lens combination 40 and 80. An additional lens may be included in the view finder cover 54 for assisting in converting the view finder into optics compatible with the close up lens.

The sterilization or disinfection of disposable camera 10 can be accomplished in a number of conventional manners. It is best and most practical to treat the camera as a "semi-critical device" under the guidelines of the Center for Disease Control. These guidelines set forth criteria for use with non-disposable cameras and such criteria can be applied to disposable cameras. Instead of actual sterilization, the Center for Disease Control recommends high level disinfection.

Both the film and the housing for the camera and the parts therein could be manufactured in a sterilized or disinfected environment so as to reduce the possibility of contamination or more simply, could be disinfected after manufacture, preferably in a common area. It is also preferable that the camera is assembled in a clean room or the like, including the installation of the sterilized or disinfected film. However, sufficient sterilization can also be accomplished by maintaining a high level of cleanliness with respect to the camera parts and sterilizing or disinfecting only the casing 14. Accordingly, any threat of contamination would be locked inside the protective casing.

As discussed above, due to the closed-in nature of the inner portion of the camera, fungal growth susceptibility may be high. Therefore the inner camera shell 34, comprised of cardboard or other impregnable material, should preferably be impregnated with a fungicide.

After assembly, the camera is then preferably covered with plastic transparent casing 14. Prior to packaging, disinfection of the camera with the casing 14 thereon, is preferably accomplished by soaking the same in a disinfection solution, such as glutaraldehyde/iodine solution. After soaking, the camera should be rinsed, dried and sealed in a sterilized or disinfected envelope or shrink wrap or both for packaging the same. Accordingly, a sealed and disinfected instrument is prepared for use in contamination sensitive environments.

Camera 10 disclosed herein is preferably used like any other disposable camera. Before use, however, the shrink wrap packaging is removed from camera 10. The user of the camera simply points the view finder at the object to be photographed and presses the photography button. As discussed above, the view finder cover preferably should be used so as to avoid contamination of the view finder from the eye or surgical mask of the user. All other connections including the endoscope adapter and the close-up lens should be connected as discussed above if required for that particular procedure. In applicable situations, measuring device 18 should be used to measure the distance from camera lens 40 to the object. As such, the user of the camera could position himself correctly so as to obtain a high quality, high resolution photograph of the object and/or connect the close up lens attachment to the camera. The film may then be removed and processed and the camera thrown away.

As an alternative to disposable cameras, it is contemplated that a non disposable camera may be provided having the aforementioned design features including, most importantly, the protective casing which is highly susceptible to disinfection.

The primary advantage of this invention is that a disinfected and disposable still frame camera is provided which may be used safely in areas which are highly sensitive to contamination. Another advantage of this invention is that a disposable and disinfected still frame camera is provided which includes additional connections for converting and attaching the camera to optical medical instruments which allow for use of the camera in taking photographs of otherwise inaccessible areas. An additional advantage of this invention is that a disposable and disinfected camera is provided which is inexpensive to manufacture and, accordingly, purchase, while still including all necessary features. An even further advantage of this invention is that a disposable and disinfected photographic system may be provided which includes the disposable disinfected camera enclosed by a protective disinfected casing arranged in a sterilized or disinfected package for delivery to hospitals or the like requiring the use of such a system. It is apparent that there has been provided in accordance with this invention a disinfected and disposable still frame camera which fully satisfies the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modification, and variations as fall within the spirit and broad scope of the appended claims.

What is claimed is:

1. A disposable, single-use type still frame camera for use in contamination sensitive applications and environments, comprising:

a disposable, single-use type inner camera portion means for securing still frame film, exposing frames of said film and advancing said film;

a disposable, single-use type camera housing which encloses said inner continuous camera portion means;

a continuous fluid impervious, sterilized, disinfected and flexible transparent plastic material encasing said camera housing for protecting said camera and the environment from contamination, said plastic material closely fit to substantially the entirety of said camera housing;

a view finder attached to said camera housing, said view finder extending substantially outwardly from said camera housing at a distance which allows substantial separation of the camera user from the camera housing, said view finder including a body portion and a viewing portion; and a disposable view finder cover means for covering said body portion and view portion of said view finder and protecting said view portion and camera from contamination, said view finder cover means including tab means extending therefrom for assisting the release of said view finder cover means from said view finder.

2. The camera according to claim 1, wherein said casing means is disinfected.

3. The camera according to claim 1, wherein said inner camera portion means comprises an inner shell treated with a fungicide for controlling fungal growth.

4. The camera according to claim 1, wherein said view finder cover means comprises a substantially transparent cover having a mating surface for engaging said body portion.

5. The camera according to claim 1, wherein said inner camera portion means includes a lens and said camera further comprises adapter and conversion means for converting the optics of an optical instrument for compatibility with the lens of said inner camera portion means and for connecting said camera to said optical instrument.

6. The camera according to claim 5, wherein said optical instrument is an endoscope.

7. The camera according to claim 5, wherein said adapter and conversion means comprises a lens arrangement, said arrangement being designed to clearly transmit an image from the optics of said optical instrument to the lens of said camera.

8. The camera according to claim 7, wherein said adaptor and conversion means further comprises a body portion which encloses said lens arrangement, said body portion having clamp means for connection to said optical medical instrument.

9. The camera according to claim 8 wherein said body portion has rods extending therefrom for engaging said camera housing such that said lens arrangement is aligned with said camera lens, said camera housing including openings therein for receiving said rods.

10. The camera according to claim 1, further comprising first measuring means connected with said camera housing for measuring the distance from said camera to an object.

11. The camera according to claim 10, wherein said first measuring means comprises a spring loaded reel having an extendible and retractable measuring tape wound thereon.

12. The camera according to claim 10, further comprising second measuring means attached with said first measuring means for measuring the size of said object.

13. The camera according to claim 12, wherein said second measuring means comprises a cross-piece having distance measuring markings thereon.

14. The camera according to claim 13, wherein said first measuring means has a free end, said cross piece attached to said free end and substantially traversing said first measuring means.

15. The camera according to claim 1, further comprising a close-up lens attachment including means for connection to said camera housing and a lens designed to allow for focused exposure of an object from a close distance.

16. The camera according to claim 15, wherein said lens attachment further comprises a supplemental view finder lens which allows viewing by the photographer of said object being photographed at said close distance.

17. The camera according to claim 15, wherein said means for connection includes rods extending from said lens attachment and said camera housing includes openings therein for receiving said rods.

* * * * *